United States Patent [19]

Schreiber et al.

[11] Patent Number: 5,231,981
[45] Date of Patent: Aug. 3, 1993

[54] DISPLAY PANEL WITH PISTOL GRIP FOR USE WITH ANESTHESIA APPARATUS

[75] Inventors: Peter J. Schreiber, Allentown; Joachim M. Schreiber, Harleysville, both of Pa.

[73] Assignee: N.A.D., Inc., Telford, Pa.

[21] Appl. No.: 672,462

[22] Filed: Mar. 20, 1991

[51] Int. Cl.$^5$ .................. A62B 7/00; G06F 15/00; G09G 3/02
[52] U.S. Cl. .................. 128/205.23; 128/204.21; 128/204.23; 364/DIG. 1; 364/224.6; 364/DIG. 2; 364/922; 364/413.03; 273/DIG. 28; 340/709
[58] Field of Search .................. 128/204.21, 205.23, 128/204.23, 716, 710, 660.04, 660.1, 671, 688, 689, 200.24, 203.12, 203.13, 203.14, 204.18; 340/712, 709; 273/DIG. 28; 364/413.03, 224.6, DIG. 1, 922.3, DIG. 2, 927.2

[56] References Cited

U.S. PATENT DOCUMENTS

| | | | |
|---|---|---|---|
| 2,068,177 | 1/1937 | Henion | 128/203.13 |
| 3,414,896 | 12/1968 | Glick et al. | 128/205.23 |
| 4,345,612 | 8/1982 | Koni et al. | 128/203.14 |
| 4,614,186 | 9/1986 | John | 128/205.23 |
| 4,825,157 | 4/1989 | Milkan | 340/709 |
| 4,833,625 | 5/1989 | Fisher et al. | 340/728 |
| 4,895,376 | 1/1990 | Chiang Shiung-Fei | 273/434 |
| 4,957,107 | 9/1990 | Sipin | 128/204.18 |
| 4,975,689 | 12/1990 | Suzuki et al. | 340/709 |
| 5,065,146 | 11/1991 | Garrett | 340/709 |

FOREIGN PATENT DOCUMENTS 9009771 9/1990 World Int. Prop. O. ............ 600/22

*Primary Examiner*—Edgar S. Burr
*Assistant Examiner*—Kimberly L. Asher
*Attorney, Agent, or Firm*—Caesar, Rivise, Bernstein, Cohen & Pokotilow, Ltd.

[57] ABSTRACT

A control/display assembly for controlling and visually displaying operating conditions/functions of an associated apparatus, e.g., an anesthesia machine. The control/display assembly comprises a panel, e.g., screen, which is arranged to be manually moved and oriented with respect to the apparatus for the user's convenience and a pistol grip having a trigger and a rotary selector member mounted thereon. The pistol grip is arranged to be readily held in the hand of the user to move the panel to the desired position and/or orientation and to hold it stationary while the selector member and trigger are operated. The rotary selector is arranged to be rotated by the thumb of the user to move a cursor on the screen to a desired display/function. The trigger is arranged to be depressed by the user's finger to select a desired display/function.

14 Claims, 3 Drawing Sheets

DISPLAY PANEL WITH PISTOL GRIP FOR USE WITH ANESTHESIA APPARATUS

This invention relates generally to medical apparatus, e.g., anesthesia machines, and more particularly to manually positionable control/display panels for controlling the operation of such apparatus and for providing a visual display of various data.

BACKGROUND OF THE INVENTION

Various types of anesthesia machines have been disclosed in the patent literature and many are available commercially today. Heretofore such machines have made use of various types of control and display panels to effect the operation of the machine and to provide visual indications of various operating conditions/functions of the machine as well as monitored patient data, e.g., pulse rate, oxygen saturation, blood pressure, etc. Such panels and their associated actuators, e.g., buttons, switches, etc. have typically been located at fixed position or location on the machine.

Such fixed or stationarily positioned control/display panels leave something to be desired from the standpoint of ease of use, convenience, and accessibility. Thus, it is desirable to provide a control/display panel which can be readily positioned with respect to the user and without moving the anesthesia machine itself so that the panel can be located at a convenient position and orientation for use.

OBJECTS OF THE INVENTION

Accordingly, it is the general object of this invention to provide a control panel for any type of controllable apparatus, e.g., an anesthesia machine, which overcomes the disadvantages of the prior art.

It is a further object of this invention to provide a control panel for apparatus which can be readily moved to a desired position and orientation with respect to the apparatus for effecting the convenient operation of the apparatus via the control panel.

It is another object of this invention to provide a display panel for apparatus which can be readily moved to a desired position and orientation with respect to the apparatus to provide a visual display of various operating parameters and for enabling the user to select the desired visual display thereat.

It is still another object of this invention to provide a control and/or display panel for apparatus which can be readily moved to a desired position and orientation and which can be held stationary by the user while manual inputs are provided thereto.

It is yet another object of this invention to provide a control and display panel for an anesthesia machine which can be readily moved to a desired position and orientation and which can be held by the user at that position so that he/she may readily control the operation of the machine from said panel.

SUMMARY OF THE INVENTION

These and other objects of the instant invention are achieved by providing a control panel for enabling at least one manual input to be provided to an associated piece of apparatus, e.g., an anesthesia machine, to control the operation thereof. The panel is mounted on the apparatus so that it can be readily moved with respect thereto to a convenient position for use by the user of the apparatus. The control panel comprises handle means and associated actuator means.

The handle means is arranged to be readily gripped by the user to hold the control panel stationary. The actuator means is arranged to be operated by the user when the panel is stationary to provide the input to the apparatus.

In one preferred embodiment of the apparatus the control panel includes a screen for visually displaying various operations/functions of the apparatus. In that embodiment the handle means is in the form of a pistol grip, and the actuator means is in the form of rotatable selector and a trigger mechanism mounted on the pistol grip. The rotatable selector switch is arranged to be operated by the user's thumb when the pistol grip is in the user's hand to effect some change in the display/operation of the machine, e.g., to move a cursor on the screen to a desired operation/function, to change a displayed value, or effect some other operation. The trigger mechanism is arranged to be operated by the user's finger when the pistol grip is in the user's hand to effect some operation or change in the display or operation of the machine, e.g., to move a cursor on the screen to a desired operation/function, to initiate a selected operation/function, etc.

DESCRIPTION OF THE DRAWING

Other objects and many of the attendant advantages of this invention will be readily appreciated as the same becomes better understood by reference to the following detailed description when considered in connection with the accompanying drawing wherein.

DETAILED DESCRIPTION OF THE PREFERRED EMBODIMENT

Figure 1:
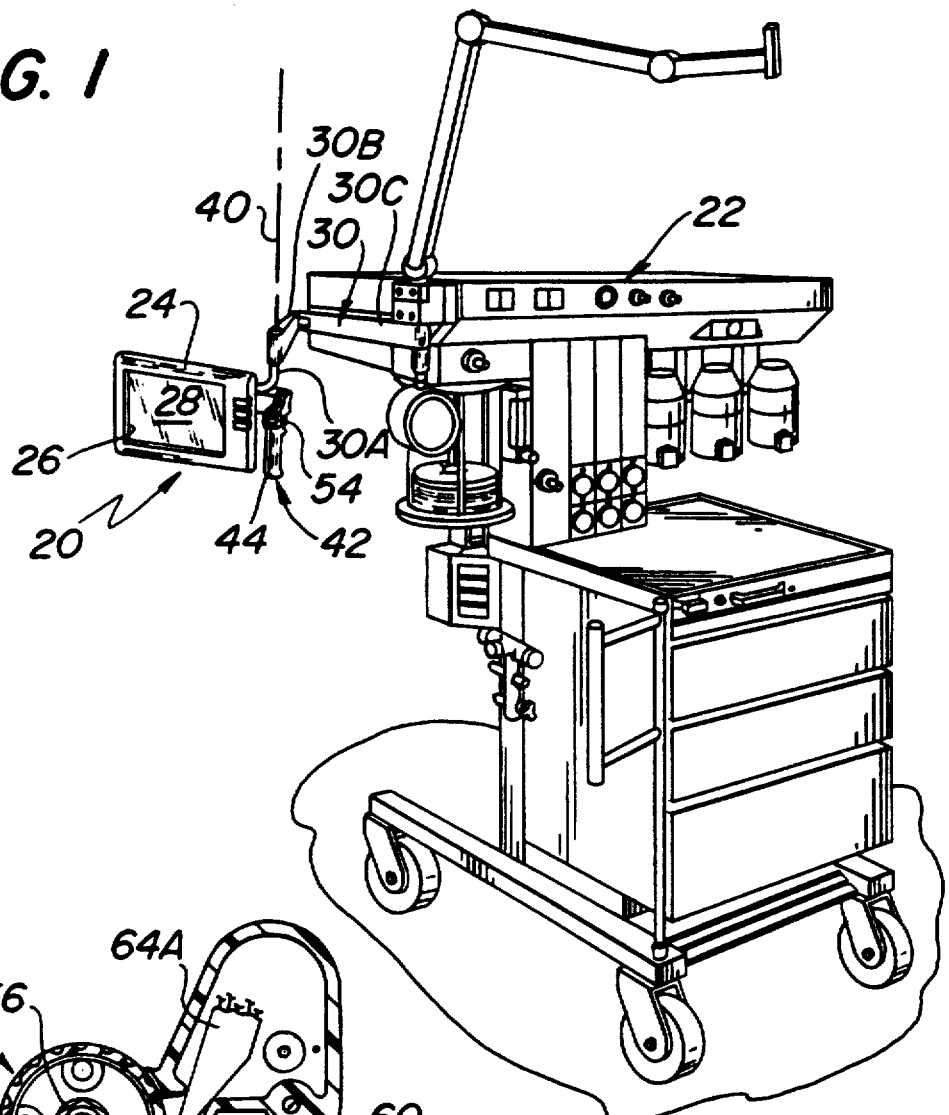
FIG. 1 is a perspective view of an anesthesia machine utilizing a control/display panel constructed in accordance with this invention.

Referring now in detail to the drawing wherein like reference characters refer to like parts, there is shown at 20 in FIG. 1 a control/display panel assembly constructed in accordance with the subject invention. The assembly 20 is particularly suited for use as an input device for an anesthesia machine 22, but can be used with any type of controllable apparatus, medical or other, where it is desirable to have a control and/or display panel which can be moved or oriented to various positions for convenient access and viewability by the user of the apparatus.

The control/display panel assembly 20 basically comprises a hollow housing 24 having a window 26 (FIGS. 1 and 3) in which a display panel, e.g., an electroluminescent screen, 28 is mounted. In a commercial embodiment of this invention the panel is a conventional device, such as that sold by Finlux under the part number designation MD640.40052.

Figure 2:
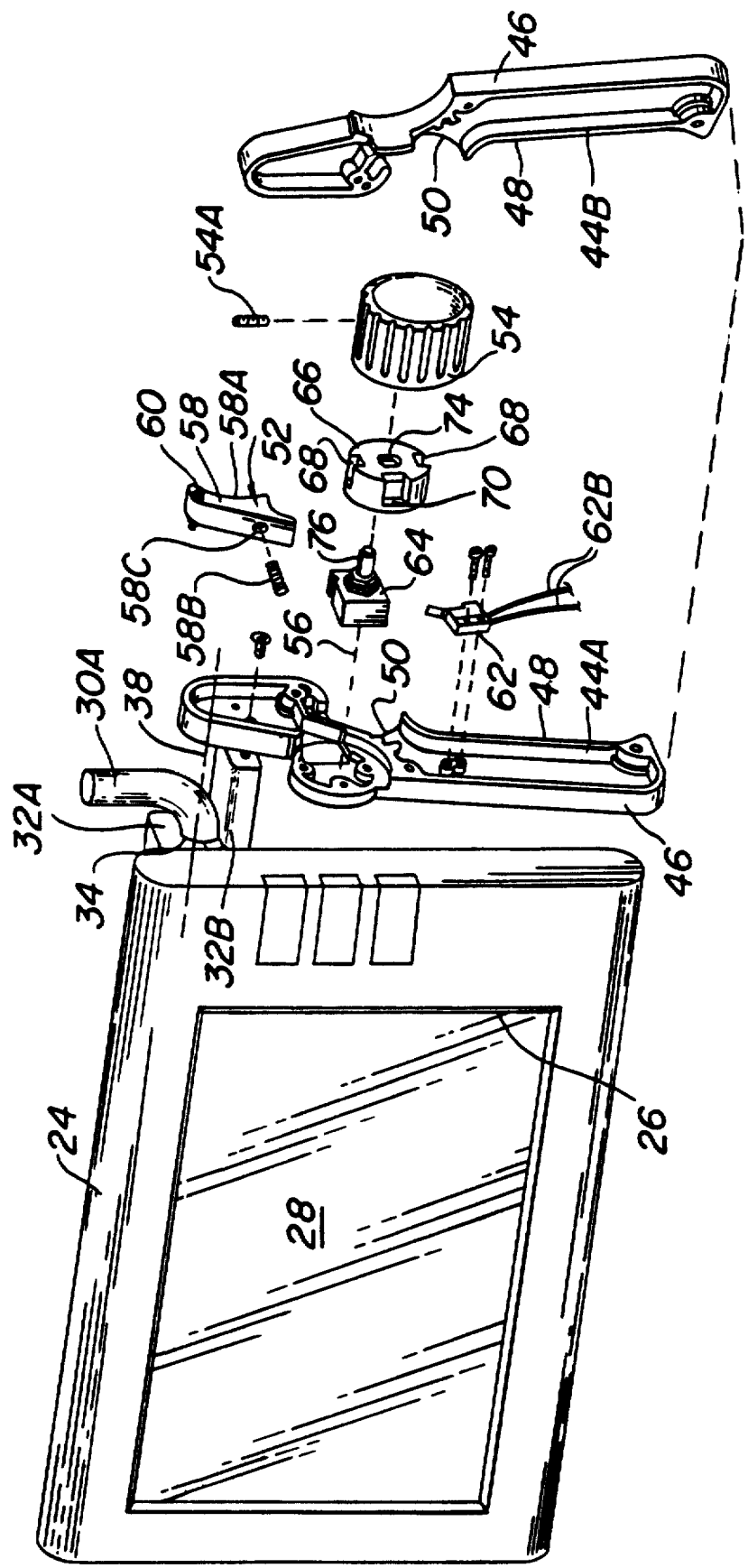
FIG. 2 is a perspective view, partially exploded, of the control/display panel shown in FIG. 1.

The housing 24 is mounted on a moveable (e.g., articulated) arm 30 via a mounting bracket formed of two components 32A and 32B (FIG. 2). The bracket component 32B is fixedly secured to the rear of the housing 24. The arm 30 includes an L-shaped, rod-like arm section 30A having a horizontally oriented portion which is disposed within an opposed pair of grooves 34 in the bracket components 32A and 32B. The bracket components 32A and 32B are secured together via respective threaded fasteners (not shown) extending through aligned holes in the bracket components. The grooves 34 form a passageway in which the horizontal portion of the arm section 30A is journalled so that the arm section may be rotated therein to tilt the panel 20 with respect to a horizontal axis 38 centered through the passageway. That arm section is itself arranged to be pivoted about a vertical axis 40 extending through a joint at the end of another section 30B of the arm 30. The arm section 30B is in turn pivotally connected to another arm section 30C.

Accordingly, the panel 20 can be pivoted about any vertical axis, such as axis 40, and the arm sections extended to enable the panel assembly 20 to be positioned at various locations with respect to the machine 22 so that the user of the machine may have ready access to it.

In order to facilitate the movement/positioning of the panel assembly 20 to the desired position/orientation the assembly 20 includes handle means 42. That means basically comprises an ergonomically shaped pistol-like hand grip 44 fixedly secured to the housing 24 via the bracket section 32B. The hand grip 44 is made up of a pair of sections 44A and 44B which are secured together and to the bracket section 32A via plural threaded fasteners (not shown).

When the two sections 44A and 44B are secured together the resulting hand-grip 44 includes a front side 46 and a rear side 48. An arcuate recess 50 is located on the rear side of the hand grip at the upper end thereof. A trigger mechanism 52 is located within the recess 50 so that it can be actuated, e.g., depressed, by the user's index finger when he/she grasps the hand grip 44. A rotatable selector wheel 54 is mounted on the front side 46 of the hand grip 44 generally opposite to the trigger mechanism so that it can be rotated by the user's thumb when he/she grasps the hand grip. To that end the wheel is arranged to be rotated about a horizontal axis 56 extending parallel to the axis 38 and perpendicularly to the longitudinal axis of the hand grip 44. Movement of the wheel is readily achieved by placing one's thumb on it and pivoting the thumb vertically up or down.

The trigger mechanism and the rotatable selector wheel are arranged to be manually operated by the user to input commands or instructions to the anesthesia machine 22 to control its operation and/or the control and display of various information and/or data. The details of the construction and operation of the trigger mechanism and the rotatable selector wheel will now be described.

Figure 4:
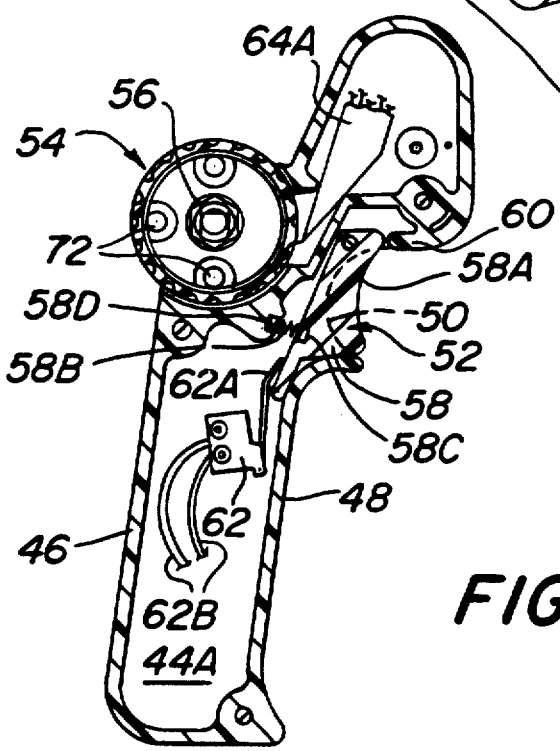
FIG. 4 is an enlarged sectional view taken along line 4—4 of FIG. 3.

As can be seen clearly in FIGS. 2 and 4 the trigger mechanism basically comprises a button or trigger element 58 having an ergonomically shaped arcuate surface 58A arranged to be engaged by the user's index finger. The trigger element 58 is pivotally mounted within aligned openings in the two hand grip sections 44A and 44B via a pivot pin 60. A conventional electrical microswitch 62 is mounted within the grip sections 44A and 44B adjacent the trigger element via a pair of screws. The trigger element is biased outward by a compression spring 58B located within a hole 58C in the rear of the trigger element and a corresponding hole 58D in the hand grip section 44A. Thus, when the trigger element is depressed (pulled back) it pivots inward slightly to engage the microswitch's actuating lever 62A to close the contacts (not shown) in the microswitch, thereby providing an electrical signal, via conductors 62B, to the interior of the control/display panel assembly 20 (and from there to the machine 22).

The selector or "thumb" wheel 54 is coupled to means (to be described hereinafter) for providing electrical signals to the interior of the control/display panel assembly and from there to the machine 22. That means basically comprises a conventional optical shaft encoder 64, such as that sold by Hewlett Packard Company under the part designation HPRG-AD32 #13C. The encoder 64 is fixedly mounted within the hand grip section 44A under a cover 66. The cover 66 basically comprises a hollow disk-shaped member having a plurality, e.g., three, recesses or notches 68 at 90 degree spaced apart locations in its periphery. Each recess includes an aperture 70 therein through which a respective threaded fastener (not shown) extends into a corresponding hole 72 in the hand grip section 44A to secure the cover to the hand grip section. The cover includes a central opening 74 through which the rotatable shaft 76 of the optical encoder 64 extends. That shaft is fixedly secured via a set screw 54A to the thumb wheel so that rotation of the thumb wheel about axis 56 effects the concomitant rotation of the encoder's shaft.

The optical encoder is arranged to provide output signals via a ribbon conductor 64A (FIG. 4) upon the rotation of the thumb wheel 54 in either rotational direction about axis 56. Thus, in one exemplary embodiment of this invention turning the thumb wheel 54 vertically upwards produces an "increment" (i.e., increase) signal, while turning the wheel vertically downward produces a "decrement" (i.e., decrease) signal. These signals are utilized by the assembly 20 and the machine 22 to effect various operations/displays. Examples of such action will be described with reference to FIG. 3 and is a function of the specific software in the machine 22.

Figure 3:
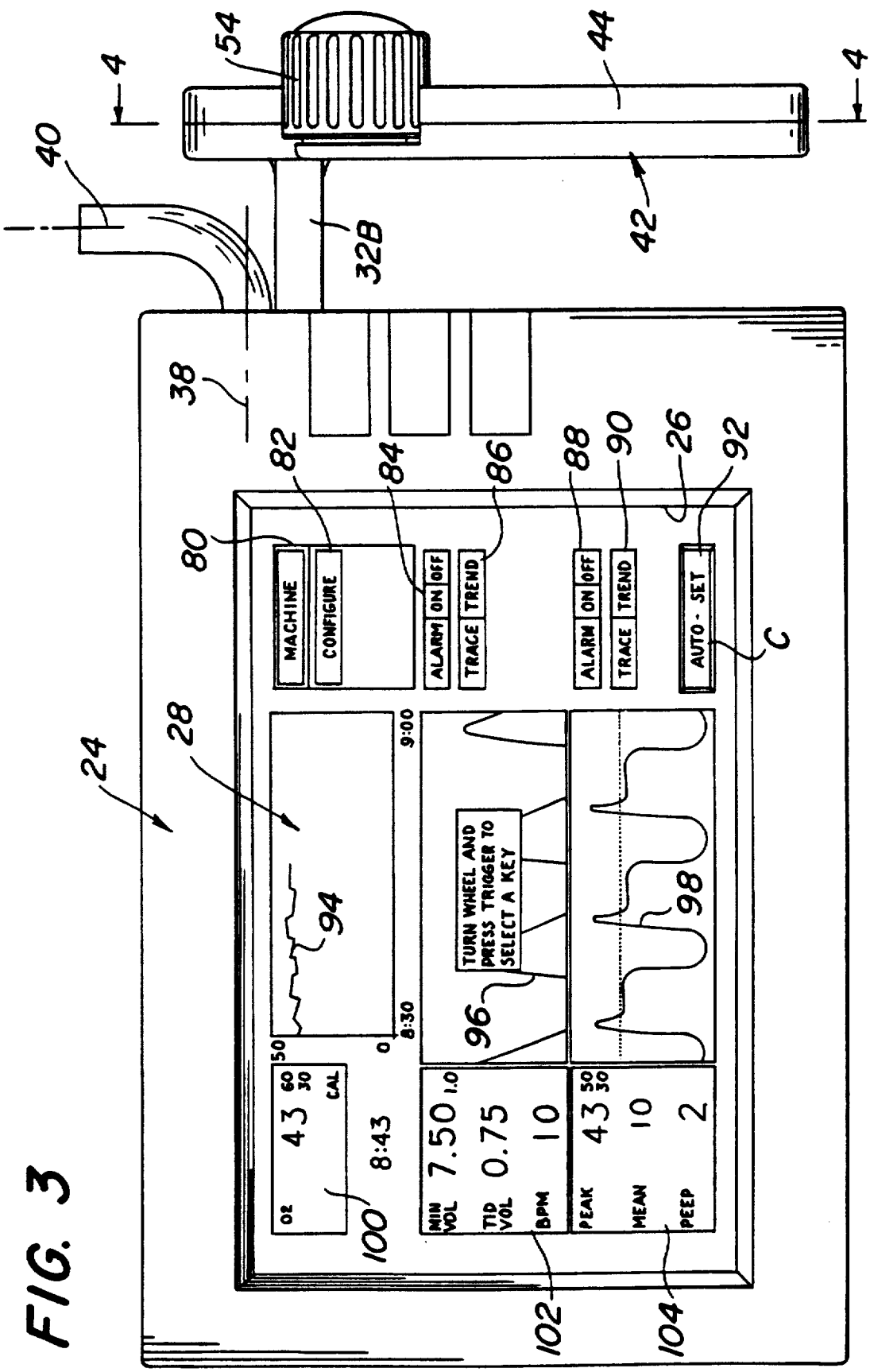
FIG. 3 is an enlarged front elevational view of the control panel shown in FIG. 2.

Referring now to FIG. 3, the operation of the control/display assembly 20 will now be described with respect to usage of the anesthesia machine 22. In particular FIG. 3 shows the display panel, e.g., screen, 28 as it appears in one exemplary mode of operation, i.e., a "select" mode, wherein predetermined system/patient data and machine options or functions are displayed for user selection (input) via the control/display assembly 20. As will be appreciated from the discussion to follow the control/display assembly 20 essentially constitutes the remote control/display for the machine by providing the user with a comprehensive display of vital information.

Operation of the control/display assembly 20 is as follows. The user grasps the hand (pistol) grip in his/her hand to move the panel to a desired convenient position/orientation. With the pistol grip in the user's hand he/she then places his/her index finger on the trigger and his/her thumb on the thumb wheel to sequence through various operations of the machine as selected by the user. In this regard, when the control/display is in a "select" mode, the visual displays on the screen will be as shown in FIG. 3.

Thus as can be seen when the control/display assembly 20 is in the "select" mode, its screen displays various key-like representations or "icons" thereon. These icons have the appearance of a conventional touch key and are hence referred to hereinafter as "soft keys". Each soft key includes a legend therein describing a specific function that the machine 22 or the control/display assembly 20 will perform upon selection of that soft key. In the "select" mode the soft keys displayed on screen 28 are a "machine" soft key 80, a "configure" soft key 82, an "alarm on/off" soft key 84, a "trace/trend" soft key 86, an "alarm on/off" soft key 88, a "trace/trend" soft key 90, and an "auto-set" soft key 92. To the left of those soft keys are three graphs 94, 96, and 98, of system/patient parameters/conditions. Thus, the upper graph 94 represents the oxygen concentration trend during a designated time period, e.g., of 8:30 to 9:00 o'clock. The middle graph 96 represents the tidal volume, while the lower graph 98 represents the patients' ventilation pressure. To the left of each of the graphs are displays of data corresponding to the graphs. Thus, to the left of the oxygen concentration trend graph 94 is a box 100 displaying oxygen concentration data/limits then extant, i.e., present concentration ("43"), the upper limit of the oxygen concentration ("60"), and the lower limit ("30"). To the left of the tidal volume graph 96 is a box 102 displaying various data relating to that graph. In a similar manner to the left of the ventilation pressure graph 98 is a box 104 displaying the data relating to that graph.

Incrementing the thumb wheel moves a cursor, e.g., a highlighted or brightly illuminated box-like icon C (shown in FIG. 3 located on the auto-set soft key 92) sequentially through the soft keys so that the user can operate the machine as desired. For example, when the cursor is on the "machine" soft key 80 rotating the thumb wheel downward moves the cursor to the "configure" soft key 82. Further rotation of the thumb wheel in that direction moves the cursor to the "alarm on/off" soft key 84. Should the user wish the machine 22 to provide a tidal volume alarm, when cursor is on the soft key 84 the trigger is then depressed to move (toggle) the cursor to the alarm on soft key portion (if it isn't on that soft key portion already). This action enables that alarm function. If no alarm is desired the trigger is depressed to toggle the alarm to the "off" portion of the soft key, thereby disabling the tidal volume alarm. Further rotation of the thumb wheel in the increment direction then moves the cursor to the trace/trend soft key 86. Should the user of the machine wish to display the monitored respiratory flow data in graphical form over a short period of time, the trigger is pulled (depressed) when the cursor is on the "trace" portion of the soft key 86. A graphical display like that designated by the reference number 94 is produced. In the event it is desired to display that parameter over a longer period of time to represent a trend in that parameter, the trigger is again pulled to move (toggle) the cursor to the "trend" portion of the soft key 86, whereupon the trend of that parameter over time is displayed graphically. Incrementing the thumb wheel then moves the cursor to the alarm on/off soft key 88 to set or disable a maximum ventilation pressure alarm. The selection of whether the alarm is on or off is affected by pulling the trigger to toggle cursor to the soft key back portion for the desired function. Incrementing the thumb wheel then moves the cursor to the trace/trend soft key 90 to enable the user to select the ventilation pressure display in either the trace mode (as shown by 98) or the trend mode by suitable depression (toggling) of the trigger to either the trace or trend function. Incrementing the thumb wheel next moves the cursor to the auto-set function soft key 92. This function establishes the ventilation pressure alarm threshold at a predetermined value, e.g., 4 cm below peak pressure. Further, incrementing of the thumb wheel causes the cursor to move to the data display box 100 and in particular to the upper limit value of the oxygen concentration to allow the user to adjust that value, if desired. To achieve that end the user merely pulls the trigger when the cursor is on the upper limit of the oxygen concentration. The value may now be changed. Thus to set or adjust that value from the value presently displayed (e.g., "60"), all that is necessary is to increment or decrement the thumb wheel to raise or lower that limit, respectively, as desired. Establishment of the low limit for the oxygen concentration is effected in a similar manner. If it is desired to calibrate the oxygen sensor, the thumb wheel is incremented to move the cursor to the "cal" soft key, whereupon the trigger is then depressed to effect the calibration of the oxygen sensor.

Operation of the control/display assembly 20 to effect adjustment of the alarm limits of tidal volume, ventilation pressure, etc. is accomplished in a similar manner to that described heretofore by use of the thumb wheel and trigger.

Without further elaboration, the foregoing will so fully illustrate our invention that others may, by applying current or future knowledge, readily adopt the same for use under various conditions of service.

We claim:

1. Anesthesia apparatus comprising an anesthesia machine, a control panel for said machine, and an arm mounting said control panel on said machine, said control panel providing plural predetermined visual displays of medical information, said control panel comprising selectably operable actuator means for providing at least one manual input to said machine to control the operation thereof, said arm being movable whereupon said panel can be readily moved towards and away from said machine and in plural directions with respect to a first axis and in plural directions with respect to a second axis, said second axis being perpendicular to said first axis so that said panel is at a desired distance from said machine and is at a desired orientation for convenient use by the user of said apparatus, said control panel comprising handle means coupled to said actuator means, said handle means including a handle portion configured to be readily gripped in one hand of the user to move said panel with respect to said axes to said desired distance from said machine and said desired orientation, said actuator means being pressable by one finger of the hand of the user when said handle means is gripped in that hand for providing said input to said apparatus and for causing said panel to display a selected one of said visual displays, whereupon the holding of said handle portion in said hand of said user prevents unwanted movement of said panel when said actuator means is pressed.

2. The apparatus of claim 1 wherein said handle means is in the shape of a pistol grip and wherein said actuator means comprises a trigger-like member mounted on said pistol grip.

3. The apparatus of claim 1 wherein said visual display comprises selectable options for the operation of said apparatus and wherein said actuator means additionally comprises selectable means coupled to said handle means and actuatable by a second finger of the hand of the user when gripping said handle means for selecting a desired option for the operation of said apparatus.

4. The apparatus of claim 3 wherein said selectable means comprises a member which is mounted for rotation with respect to said handle means.

5. The control panel of claim 4 wherein said rotatable member comprises a shaft encoder.

6. The apparatus of claim 4 wherein said handle means comprises a pistol grip having a front portion and a rear portion, said actuator means comprises a trigger-like member mounted on said front portion of said pistol grip for pressing by said one finger, and wherein said rotatable member is mounted on said rear portion of said pistol grip for engagement and movement by the thumb of said hand.

7. The control panel of claim 6 wherein said rotatable member comprises a shaft encoder.

8. Medical apparatus comprising a machine, a control panel for said machine, and an arm mounting said control panel on said machine, said control panel providing visual displays of medical information, said control panel comprising handle means and selectably operable actuator means, said selectively operably actuator means for providing at least one manual input to said apparatus to control the operation thereof, said arm being movable toward and away from said machine and in plural directions with respect to a first axis and in plural directions with respect to a second axis, said second axis being perpendicular to said first axis so that said panel is at a desired distance from said machine and at a desired orientation for convenient use by the user of said apparatus, said handle means comprising a pistol grip configured to be held in the hand of the user of said apparatus and having a front portion and a rear portion, said pistol grip being arranged to move said arm with respect to said axes said actuator means comprising first engagable means located on said front portion of said pistol grip for engagement by one finger of the hand holding the pistol grip, and second engagable means mounted on the rear portion of said pistol grip for engagement by the thumb of that hand, at least one of said first and second engagable means providing said input to said apparatus when engaged, and whereupon the holding of said handle portion in that hand prevents unwanted movement of said panel when said engagable means is engaged.

9. The apparatus of claim 8 wherein said machine comprises an anesthesia machine.

10. The apparatus of claim 9 wherein said panel provides a visual display of selectable options for the operation of said apparatus, and wherein one of said engagable means selects a desired one of the selectable options for the operation of said apparatus.

11. The apparatus of claim 10 wherein said first engagable means comprises a trigger-like member, and wherein said second engagable means comprises a rotatable member.

12. The apparatus of claim 11 wherein said rotatable member comprises a shaft encoder.

13. The apparatus of claim 9 wherein said first engagable means comprises a trigger-like member, and wherein said second engagable means comprises a rotatable member.

14. The apparatus of claim 13 wherein said rotatable member comprises a shaft encoder.

* * * * *